United States Patent
Ikeda et al.

(10) Patent No.: US 9,023,622 B2
(45) Date of Patent: May 5, 2015

(54) METHOD FOR PRODUCING L-AMINO ACID USING A MICROORGANISM WITH DECREASED ASPARTATE AMINOTRANSFERASE ACTIVITY

(75) Inventors: Hajime Ikeda, Ibaraki (JP); Makoto Yagasaki, Yamaguchi (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 136 days.

(21) Appl. No.: 13/148,625

(22) PCT Filed: Feb. 9, 2010

(86) PCT No.: PCT/JP2010/051905
§ 371 (c)(1),
(2), (4) Date: Sep. 6, 2011

(87) PCT Pub. No.: WO2010/092959
PCT Pub. Date: Aug. 19, 2010

(65) Prior Publication Data
US 2011/0312042 A1    Dec. 22, 2011

(30) Foreign Application Priority Data
Feb. 10, 2009   (JP) .................................. 2009-028693

(51) Int. Cl.
*C12P 13/24*   (2006.01)
*C12P 13/14*   (2006.01)
*C12P 13/10*   (2006.01)
*C12N 9/10*   (2006.01)

(52) U.S. Cl.
CPC .............. *C12N 9/1096* (2013.01); *C12P 13/10* (2013.01); *C12P 13/14* (2013.01); *C12P 13/24* (2013.01); *C12Y 206/01001* (2013.01)

(58) Field of Classification Search
CPC ........ C12N 1/20; C12N 9/1096; C12N 15/00; C12N 15/01; C12P 13/10; C12P 13/14; C12P 13/24; C12Y 206/01001
USPC ............. 435/193, 107, 110, 114, 252.33, 471
See application file for complete search history.

(56) References Cited

U.S. PATENT DOCUMENTS

| 5,316,943 | A | * | 5/1994 | Kidman et al. ............... 435/280 |
| 6,004,773 | A | | 12/1999 | Araki et al. |
| 6,316,262 | B1 | * | 11/2001 | Huisman et al. ............. 435/490 |
| 6,455,284 | B1 | * | 9/2002 | Gokarn et al. ............... 435/71.2 |
| 2005/0282258 | A1 | * | 12/2005 | Jayaraman et al. ......... 435/114 |

FOREIGN PATENT DOCUMENTS

| EP | 0 152 275 | A2 | 8/1985 |
| EP | 0 219 027 | A2 | 4/1987 |
| EP | 0 293 514 | A1 | 12/1988 |
| EP | 1 479 775 | A1 | 11/2004 |
| JP | 60-184394 | A | 9/1985 |
| JP | 06-102028 | A | 4/1994 |
| JP | 10-215883 | A | 8/1998 |
| WO | WO 03/072786 | A1 | 9/2003 |

OTHER PUBLICATIONS

Gelfand et al., J. Bacteriol. 130:429-440, 1977.*
Jantama et al., Biotechnol. Bioengineer. 101:881-893, 2008.*
Fotheringham et al., Biochem. J. 234:593-604, 1986.*
Fotheringham et al., Biotechnol. Prog. 7:380-381, 1991.*
Bank et al., Analytical Biochem. 240:167-176, 1996.*
Back et al., J. Gen. Microbiol. 27:41-50, 1962.*
Merriam-Webster online dictionary definition of "efficiently", obtained from www.merriam-webster.com/dictionary/efficiently, last viewed on Mar. 30, 2012, 1 page.*
Hwang et al., J. Mol. Cat. B: Enzymatic 37:47-55, 2005.*
Kondo et al., *Biochemical and Biophysical Research Communications*, 122(1): 62-67 (1984).
Malcolm et al., *Biochemical and Biophysical Research Communications*, 132(3): 915-921 (1985).
Neidhardt et al. (ed.), *Escherichia coli and Salmonela typhimurium*, Second Edition, ASM Press, Washington, D.C. (1987), pp. 314-321.
Shio et al., *Agric. Biol. Chem.*, 46(2): 493-500 (1982).
Japanese Patent Office, International Search Report in International Patent Application No. PCT/JP2010/051905 (Mar. 16, 2010).
Rothman et al., *J. Mol. Biol.*, 327: 593-608 (2003).
Shibasaki et al., *Journal of Bioscience and Bioengineering*, 90(5): 522-525 (2000).
European Patent Office, Communication Pursuant to Article 94(3) EPC in European Patent Application No. 10 741 236.3 (Jul. 18, 2013).
Wolfman et al., *Journal of Clinical Investigation*, 100(2): 321-330 (1997).
Lin et al., "Aspartate aminotransferase [*Arabidopsis thaliana*]," Database Geneseq (GenBank), Database Accession No. AEC07285.1 (Jun. 13, 2011).
European Patent Office, Extended European Search Report in European Patent Application No. 10741236.3 (Jul. 26, 2012).

* cited by examiner

*Primary Examiner* — David J Steadman
(74) *Attorney, Agent, or Firm* — Leydig, Voit & Mayer, Ltd.

(57) ABSTRACT

According to the present invention, a process for producing an amino acid using a microorganism in which aspartate aminotransferase activity is decreased or deleted, and which has the capability of producing and accumulating the amino acid is provided.

2 Claims, No Drawings

METHOD FOR PRODUCING L-AMINO ACID USING A MICROORGANISM WITH DECREASED ASPARTATE AMINOTRANSFERASE ACTIVITY

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,880 bytes ASCII (Text) file named "708794SequenceListing.txt," created Aug. 9, 2011.

TECHNICAL FIELD

The present invention relates to a process for producing an amino acid using a microorganism belonging to the genus *Escherichia* in which the aspartate aminotransferase activity is decreased or lost, and which has the ability to produce and accumulate the amino acid.

BACKGROUND ART

Aspartate aminotransferase is an enzyme that catalyzes the production of aspartic acid from oxaloacetic acid and glutamic acid. While aromatic amino acid aminotransferase is known as another enzyme that catalyzes the synthesis of aspartic acid from oxaloacetic acid and glutamic acid in *Escherichia coli*, the synthesis of aspartic acid is thought to be achieved mainly by aspartate aminotransferase (Non-patent Document 1).

The biochemical properties of the aspartate aminotransferase of microorganisms of the genus *Escherichia* are known, and the aspC gene that encodes for the enzyme is also known (Non-patent Document 2). It is also known that by overexpressing the aspC gene of a microorganism of the genus *Escherichia*, the L-amino acid productivity can be improved (Patent Documents 1 and 2).

Proteins in living organisms are polymers of α-amino acids, and basically L-amino acids are the constituents of the protein. Many L-amino acids, in addition to being important as constituents of living organisms, exhibit bioactivity or pharmacological activity per se, or have a flavoring effect or a nutritive effect; a wide variety of use applications, including pharmaceuticals, foods and the like, have been developed.

However, no report is available stating or suggesting that L-amino acid production efficiency can be improved by decreasing or deleting aspC activity in the fermentative production of L-amino acids.

PRIOR ART DOCUMENTS

Patent Documents

[patent document 1] U.S. Pat. No. 6,004,773
[patent document 2] WO2003/072786

Non-Patent Documents

[non-patent document 1] *Escherichia coli* and *Salmonela*, Second Edition, Editor in Chief: F. C. Neidhardt, ASM Press, Washington D.C., 1996
[non-patent document 2] Kondo K. et al., Biochem Biophys Res Commun., 1984; 122(1):62-7

SUMMARY OF THE INVENTION

Problems to Be Solved by the Invention

A problem to be solved by the present invention is to provide a process for producing an L-amino acid using a microorganism.

Means of Solving the Problems

As a result of extensive investigations, the present inventors found that a microorganism in which aspartate aminotransferase activity is decreased compared with the parent strain or deleted exhibits improved L-amino acid production efficiency, and have developed the present invention.

Accordingly, the present invention relates to the following [1] to [6].

[1] A process for producing an L-amino acid which comprises; culturing in a medium a microorganism which has the ability to produce the L-amino acid, and in which the aspartate aminotransferase activity is decreased compared with the parent strain or deleted,
producing and accumulating the L-amino acid in a culture, and, collecting the L-amino acid from the culture.

[2] The process for producing the L-amino acid according to [1], wherein the microorganism in which the aspartate aminotransferase activity is decreased compared with the parent strain or deleted is deficient in the DNA that encodes for the aspartate aminotransferase.

[3] The process for producing the L-amino acid according to [1] or [2], wherein the aspartate aminotransferase is a protein selected from among (1) to (3) below.
(1) A protein consisting of the amino acid sequence shown in SEQ ID NO:2
(2) A protein consisting of an amino acid sequence resulting from deletion, substitution or addition of one or more amino acids in the amino acid sequence shown in SEQ ID NO:2, and having the aspartate aminotransferase activity
(3) A protein consisting of an amino acid sequence having 80% or more homology to the amino acid sequence shown in SEQ ID NO:2, and having the aspartate aminotransferase activity

[4] The process for producing the L-amino acid according to [1] or [2], wherein the aspartate aminotransferase is encoded by a DNA selected from among (1) to (3) below.
(1) DNA consisting of the nucleotide sequence shown in SEQ ID NO:1
(2) DNA that hybridizes with a DNA consisting of the nucleotide sequence complementary to the nucleotide sequence shown in SEQ ID NO:1 under stringent conditions, and that encodes for the protein having the aspartate aminotransferase activity
(3) DNA having 80% or more homology to the nucleotide sequence shown in SEQ ID NO:1, and encoding for the protein having the aspartate aminotransferase activity

[5] The process for producing the L-amino acid according to any one of [1] to [4], wherein the microorganism belongs to the genus *Escherichia*.

[6] The process for producing the L-amino acid according to any one of [1] to [5], wherein the L-amino acid is selected from the group consisting of L-glutamic acid, L-glutamine, L-proline, L-ornithine, L-citrulline, L-arginine, and L-hydroxyproline.

Effect of the Invention

The present invention enables to efficiently produce L-amino acids using microorganisms with improved L-amino acid production efficiency compared with conventional microorganisms, making it possible to efficiently provide L-amino acids that exhibit a wide variety of use applications in the fields of pharmaceuticals, health foods and the like.

MODES FOR CARRYING OUT THE INVENTION

1. Preparation of Microorganism in Which an Aspartate Aminotransferase Activity is Decreased Compared with the Parent Strain or Deleted The present invention provides a process for producing an L-amino acid using a microorganism in which an aspartate aminotransferase activity is decreased compared with the parent strain or deleted. Therefore, a microorganism used in the production method of the present invention can be obtained by decreasing or deleting the aspartate aminotransferase activity in the microorganism having the capability of producing an L-amino acid, and having the aspartate aminotransferase activity.

In the present invention, the parent strain may be any microorganism having the aspartate aminotransferase activity, whether a wild strain or a strain artificially bred from the wild strain; also, the parent strain may have the capability of producing an L-amino acid, and may not. The capability of producing an L-amino acid, possessed by the parent strain, may be one that is originally possessed by the parent strain, or may be one artificially conferred by a method described below. When the parent strain does not have the capability of producing an L-amino acid, a microorganism to be used in the method of the present invention can be acquired by, in addition to decreasing or deleting the aspartate aminotransferase activity of the parent strain, artificially conferring the capability of producing an L-amino acid by a method described below.

Parent strains include, for example, bacteria described by Neidhardt, F. C. et al. (*Escherichia coli* and *Salmonella*, Editor in Chief: F. C. Neidhardt, ASM Press, Washington D.C., 1996, (page 1201, Table 1)). Preferable parent strains include, for example, bacteria belonging to the genus *Escherichia*, the genus *Serratia*, the genus *Bacillus*, the genus *Brevibacterium*, the genus *Corynebacterium*, the genus *Pseudomonas* or the genus *Streptomyces* and the like; more preferable bacteria include *Escherichia coli*, *Corynebacterium glutamicurn*, *Corynebacterium ammoniagenes*, *Corynebacterium lactofermentum*, *Corynebacterium flavum*, *Corynebacterium eficiens*, *Bacillus subtilis*, *Bacillus megaterium*, *Serratia marcescens*, *Pseudomonas putida*, *Pseudomonas aeruginosa*, *Streptomyces coelicolor* or *Streptomyces lividans*, with greater preference given to *Escherichia coli*.

A microorganism having the capability of producing an L-amino acid can be acquired by improving a parent strain to artificially confer the capability of producing an L-amino acid by a publicly known method. The publicly known method is exemplified by:
(a) methods wherein at least one mechanism behind the control of L-amino acid biosynthesis is mitigated or cancelled,
(b) methods wherein the expression of at least one enzyme involved in L-amino acid biosynthesis is enhanced,
(c) methods wherein the number of copies of at least one enzyme gene involved in L-amino acid biosynthesis is increased,
(d) methods wherein at least one metabolic pathway that branches from the biosynthesis pathway for an L-amino acid to a metabolite other than the L-amino acid is weakened or blocked, and
(e) methods wherein a cell strain whose resistance to L-amino acid analogues is higher than that of the parent strain is selected,
and the like; the above-described publicly known methods can be used alone or in combination.

Regarding specific methods of (a) to (e) above, methods (a) above are described in Agric. Biol. Chem., 43, 105-111 (1979), J. Bacterial., 110, 761-763 (1972) and Appl. Microbial. Biotechnol., 39, 318-323 (1993) and the like. Methods (b) above are described in Agric. Biol. Chem., 43, 105-111 (1979) and J. Bacterial., 110, 761-763 (1972) and the like. Methods (c) above are described in Appl. Microbiol. Biotechnol., 39, 318-323 (1993) and Agric. Biol. Chem., 39, 371-377 (1987) and the like. Methods (d) above are described in Appl. Environ. Microbiol., 38, 181-190 (1979) and Agric. Biol. Chem., 42, 1773-1778 (1978) and the like. Methods (e) above are described in Agric. Biol. Chem., 36, 1675-1684 (1972), Agric: Biol. Chem., 41, 109-116 (1977), Agric. Biol. Chem., 37, 2013-2023 (1973) and Agric. Biol. Chem., 51, 2089-2094 (1987) and the like. With reference to the above-described documents and the like, microorganisms having the capability of producing and accumulating various amino acids can be acquired.

Furthermore, regarding how to breed a microorganism having the capability of producing and accumulating an amino acid by any one of (a) to (e) above or a combination thereof, many examples are described in Biotechnology 2nd ed., Vol. 6, Products of Primary Metabolism (VCH Verlagsgesellschaft mbH, Weinheim, 1996), section 14a, 14b, Advances in Biochemical Engineering/Biotechnology, 79, 1-35 (2003), and Aminosan Hakko, Japan Scientific Societies Press, Hiroshi Aida et al. (1986); in addition to the above, many reports are available on specific methods of breeding a microorganism having the capability of producing and accumulating an amino acid, including JP-A-2003-164297, Agric. Biol. Chem., 39, 153-160% (1975), Agric. Biol. Chem., 39, 1149-1153 (1975), JP-A-SHO-58-13599, J. Gen. Appl. Microbiol., 4, 272-283 (1958), JP-A-SHO-63-94985, Agric. Biol. Chem., 37, 2013-2023 (1973), WO97/15673, JP-A-SHO-56-18596, JP-A-SHO-56-144092, JP-T-2003-511086 and the like; with reference to the above-described documents and the like, a microorganism having the capability of producing one or more kinds of amino acids can be acquired.

The aspartate aminotransferase in the present invention can specifically be a protein consisting of the amino acid sequence shown in SEQ ID NO:2; a protein consisting of an amino acid sequence resulting from deletion, substitution or addition of one or more amino acids in the amino acid sequence shown in SEQ ID NO:2, and having the aspartate aminotransferase activity; or a protein consisting of an amino acid sequence having 80% or more homology to the amino acid sequence shown in SEQ ID NO:2, and having the aspartate aminotransferase activity.

The amino acid sequence resulting from deletion, substitution or addition of one or more amino acids in the amino acid sequence shown in SEQ ID NO:2 can be, for example, an amino acid sequence resulting from deletion, substitution or addition of 1 to 100, preferably 1 to 50, more preferably 1 to 30, still more preferably 1 to 20, most preferably 1 to 10, 1 to 5, 3, 2 or 1 amino acid.

An amino acid sequence having 80% or more homology to the amino acid sequence shown in SEQ ID NO:2 refers to, for example, an amino acid sequence having 80% or more, preferably 90% or more, more preferably 95% or more, most preferably 97%, 98% or 99% or more homology, to the amino acid sequence shown in SEQ ID NO:2. Homology of amino acid sequence can be determined using the algorithm BLAST of Karlin and Altschul [Pro. Natl. Acad. Sci. USA, 90, 5873 (1993)] or FASTA [Methods Enzymol., 183, 63 (1990)]. Based on this algorithm BLAST, programs called BLASTN and BLASTX have been developed [J. Mol. Biol., 215, 403 (1990)]. When amino acid sequences are analyzed with BLASTX on the basis of BLAST, parameters can be set to, for example, score=50 and wordlength=3. When the BLAST and Gapped BLAST programs are used, the default parameters of the respective programs can be used.

The fact that the aspartate aminotransferase activity in a microorganism used in the production method of the present invention is decreased compared with the parent strain or deleted can be determined according to a method publicly known in the art; the fact can be confirmed by, for example, measuring the aspartate aminotransferase activity in each of the microorganism used in the production method of the present invention and the parent strain by the method described in J Bacteriol., 130(1), 429-40 (1977), and comparing them.

A microorganism used in the production method of the present invention can be produced by, for example, subjecting a parent strain to a method enabling to introduce a mutation into a microorganism, such as an ordinary method of mutation treatment, gene replacement by recombinant DNA technology and the like, cell fusion, or transduction, or a method enabling to suppress the expression of the aspartate aminotransferase gene, such as the antisense method, and the like.

Methods of mutation treatment include, for example, a method using N-methyl-N'-nitro-N-nitrosoguanidine (NTG) (Biseibutsu Jikken Manyuaru, 1986, page 131, Kodansha Scientific Company), treatments with ethyl nitrosourea, benzopyrene, acridine dye or the like, ultraviolet irradiation and the like. Various alkylating agents and carcinogens can also be used as mutagens. Methods that can be used to allow a mutagen to act on cells include, for example, methods described in Soshiki Baiyou no Gijyutsu, 3rd edition (Asakura Shoten), edited by the Japanese Tissue Culture Association (1996), Nature Genetics (Nature Genet.), 314 (2000) and the like.

Methods of gene replacement based on recombinant DNA technology include a method wherein substitution, deletion or addition of one or more bases is introduced into a DNA of aspC, and the DNA is integrated into the chromosome of the parent strain by homologous recombination and the like to replace the DNA that encodes for the aspartate aminotransferase.

The DNA that encodes for the aspartate aminotransferase may be any DNA that encodes for a polypeptide having the aspartate aminotransferase activity; examples include a DNA comprising the nucleotide sequence shown in SEQ ID NO:1. DNAs of aspC include, for example, a DNA comprising the nucleotide sequence from 983741st to 984931st bases of the sequence of GenBank/EMBL/DDBJ Accession NC000913. 2, gi:49175990.

Alternatively, the DNA that encodes for the aspartate aminotransferase can be a DNA that hybridizes with a DNA consisting of a nucleotide sequence complementary to the nucleotide sequence shown in SEQ ID NO:1 under stringent conditions, and that encodes for the protein having the aspartate aminotransferase activity. Examples of stringent conditions include conditions described in Current Protocols in Molecular Biology, John Wiley & Sons, 6.3.1-6.3.6, 1999, for example, hybridization with 6×SSC (sodium chloride/sodium citrate)/45° C. followed by not less than one time of washing with 0.2×SSC/0.1% SDS/50 to 65° C.; those skilled in the art can choose as appropriate hybridization conditions that give equivalent stringency.

The DNA that encodes for the aspartate aminotransferase may also be a DNA having 80% or more homology to the nucleotide sequence shown in SEQ ID NO:1, and encoding for the protein having the aspartate aminotransferase activity. Preferably, the DNA that encodes for the aspartate aminotransferase is exemplified by a DNA having 85% or more, more preferably 90% or more, still more preferably 95% or more, still yet more preferably 97% or more, further preferably 98% or more, particularly preferably 99% or more homology, to the nucleotide sequence shown in SEQ ID NO:1. Nucleotide sequence homologies can be determined using the algorithm BLAST of Karlin and Altschul [Pro. Natl. Acad. Sci. USA, 90, 5873 (1993)] or FASTA [Methods Enzymol., 183, 63 (1990)]. When nucleotide sequences are analyzed with BLASTN on the basis of BLAST, parameters can be set to, for example, score=100 and wordlength=12.

The DNA that encodes for the aspartate aminotransferase can be acquired by a PCR method and the like, on the basis of publicly known information on the nucleotide sequence of a DNA that encodes for *Escherichia coli*-derived aspartate aminotransferase.

Methods of introducing substitution, deletion or addition of one or more bases into the DNA that encodes for the aspartate aminotransferase include, for example, methods based on the site-directed mutagenesis methods described in Molecular cloning: a laboratory manual, 3rd ed., Cold Spring Harbor Laboratory Press (2001) [hereinafter abbreviated as Molecular Cloning, Third Edition], Current Protocols in Molecular Biology, John Wiley & Sons (1987-1997) (hereinafter abbreviated as Current Protocols in Molecular Biology), and the like.

A DNA fragment comprising a gene that confers drug resistance inserted into an ORF (open reading frame) of the aspartate aminotransferase can also be prepared by a PCR method.

Methods of introducing a DNA fragment having a mutation into a parent strain include, for example, a method using phage-derived ARed recombinase [Proc. Natl. Acad. Sci. USA, 97, 6640 (2000), Mol. Microbial., 55, 137 (2005), Biosci. Biotechnol. Biochem., 71, 2905 (2007)].

By acquiring a strain that exhibits resistance to an antibiotic corresponding to an antibiotic resistance marker, a transformant harboring the recombinant plasmid integrated into the chromosome can be acquired.

Furthermore, a strain wherein the DNA that encodes for the aspartate aminotransferase on the chromosome of the parent strain is replaced by the mutated DNA can be acquired, using a method of selection based on the fact that *Bacillus subtilis* levansucrase integrated along with a mutated DNA onto the chromosome makes *Escherichia coli* sensitive to sucrose, or a method of selection based on the fact that the wild-type rpsL gene integrated into *Escherichia coli* having the streptomycin resistance mutation rpsL gene makes the *Escherichia coli* sensitive to streptomycin [Mol. Microbial., 55, 137 (2005), Biosci. Biotechnol. Biochem., 71, 2905 (2007)] and the like.

Gene replacement on the chromosome of the parent strain can be achieved by, but not limited to, the method described above; any other method of gene replacement can also be used, as far as it enables to replace a gene on the chromosome of a microorganism.

Other methods of introducing substitution, deletion, or addition into a DNA that encodes for the aspartate aminotransferase on the chromosome of the parent strain include methods utilizing a bacteriophage or conjugation; examples include methods described in Bacterial and Bacteriophage Genetics, Springer-Verlag (1981-2000).

The number of bases to which a mutation is to be introduced is not limited, as far as it is a number that allows the activity of the aspartate aminotransferase encoded by the DNA to be decreased or deleted by substitution, deletion, or addition; the number can be, for example, 1 to 300, preferably 1 to 150, more preferably 1 to 100, still more preferably 1 to 50, most preferably 1 to 30, 1 to 20, 1 to 10, 1 to 5, 3, 2 or 1.

Although the site into which a mutation is to be introduced is not always limited within the nucleotide sequence in the DNA that encodes for the aspartate aminotransferase, as far as the site allows the aspartate aminotransferase activity to be decreased or deleted by the mutation, it is preferable that the site be in the transcription/translation regulatory region of the DNA that encodes aspartate aminotransferase (hereinafter referred to as aspartate aminotransferase gene), more preferably in the nucleotide sequence possessed by the DNA that encodes aspartate aminotransferase.

Methods of introducing a base substitution to decrease or delete the aspartate aminotransferase activity include, for example, methods based on introduction of a nonsense mutation. Methods of introducing a nonsense mutation include, for example, a method wherein PCR is performed using primers comprising a stop codon and a DNA that encodes for the aspartate aminotransferase, and replacing aspC on the chromosome of the parent strain using the thus-obtained DNA that encodes for the aspartate aminotransferase, which incorporates the nonsense mutation.

Methods of decreasing or deleting aspartate aminotransferase activity by introducing a deletion of a nucleotide sequence include, for example, a method wherein the 5'-end and 3'-end of the aspartate aminotransferase gene are amplified using PCR, the fragments thus obtained are joined together by PCR to obtain the aspartate aminotransferase gene, and the gene is integrated into the chromosome, and the like.

Examples of the aspartate aminotransferase gene deprived of a nucleotide sequence include, for example, genes obtained by the method described below. First, the 5'-end of the Escherichia coli-derived aspartate aminotransferase gene is amplified using the primers of SEQ ID NO:9 or 10 and 16, and the 3'-end is amplified using the primers of SEQ ID NO:11 or 12 and 15. By performing PCR with the two amplified fragments as the templates, using the primers of SEQ ID NO:9 or 10 and 11 or 12, an aspartate aminotransferase gene lacking the 1st to 988th bases in the nucleotide sequence shown in SEQ ID NO:1 is obtained.

Aspartate aminotransferase activity can also be decreased without introducing a mutation into the aspartate aminotransferase gene. Such methods include, for example, what is called the antisense method, wherein the expression of the aspartate aminotransferase gene is suppressed by introducing into the microorganism an oligonucleotide or RNA comprising a nucleotide sequence complementary or substantially complementary to the nucleotide sequence possessed by the target mRNA that encodes for the aspartate aminotransferase, or a portion thereof, to form a specific, stable double strand with, and bind to, the target mRNA.

Although "a nucleotide sequence complementary or substantially complementary to the nucleotide sequence possessed by the target mRNA or a portion thereof" is not particularly limited with respect to the length and position thereof, as far as it is capable of binding specifically to the target mRNA, and also capable of inhibiting the translation of the mRNA to protein, it is preferable from the viewpoint of sequence specificity that the nucleotide sequence or a portion thereof comprise at least 10 bases or more, preferably about 15 bases or more, more preferably about 20 bases or more, of a portion complementary or substantially complementary to the target sequence.

Aspartate aminotransferase activity can also be decreased by introducing, in addition to an antisense RNA, a double stranded RNA consisting of an oligo-RNA complementary to the target mRNA and a strand complementary thereto (what is called siRNA) or a ribozyme to the target mRNA.

By measuring aspartate aminotransferase activity, and comparing the activity with that of the parent strain as described above, a microorganism in which an aminotransferase activity is decreased or deleted can be obtained from among the microorganisms obtained by performing the above-described operation.

2. Production Method of the Present Invention

The present invention also provides a process for producing an L-amino acid by culturing in a medium a microorganism having the capability of producing the L-amino acid, in which an aspartate aminotransferase activity is decreased compared with the parent strain or deleted, prepared by the method 1 above, to produce and accumulate the L-amino acid in the culture, and collecting the L-amino acid from the culture.

The medium used in the production method of the present invention may be a synthetic medium or a natural medium, as far as it contains nutrients such as a carbon source, a nitrogen source, minerals, vitamins and the like that are required for the growth of the microorganism of the present invention and the biosynthesis of an L-amino acid.

The carbon source may be any carbon source that can be assimilated by the microorganism used, exemplified by carbohydrates such as glucose and fructose, alcohols such as ethanol and glycerol, organic acids such as acetic acid, and the like.

Nitrogen sources include ammonia, ammonium salts such as ammonium sulfate, nitrogen-containing compounds such as amines, natural nitrogen sources such as peptone and soy hydrolysates, and the like.

Inorganic salts include potassium phosphate, magnesium sulfate, sodium chloride, ferrous sulfate, potassium carbonate and the like.

Vitamins include biotin and thiamine and the like. Furthermore, a substance required by a microorganism of the present invention for the growth thereof (for example, an amino acid required for an amino acid auxotrophic microorganism) can be added as required.

The cultivation is preferably performed under aerobic conditions such as shaking culture or deep spinner culture. Cultivation temperature is 20 to 50° C., preferably 20 to 42° C., more preferably 28 to 38° C. Cultivation pH is 5 to 9, preferably 6 to 7.5. Cultivation time is 5 hours to 5 days, preferably 16 hours to 3 days.

The L-amino acid accumulated in the culture can be collected by an ordinary method of purification. For example, the L-amino acid can be collected by ion exchange, concentration, and crystal fractionation after cell bodies and solid matter are removed via centrifugation and the like after the cultivation.

The present invention is hereinafter described specifically by means of the following Examples, to which, however, the present invention is not limited.

EXAMPLE 1

Establishment of a Strain Lacking the Aspartate Aminotransferase Gene (1) Preparation of cat-sacB Cassette A DNA fragment comprising the chloramphenicol resistance gene (cat) and the levansucrase gene (sacB) was prepared as described below.

A PCR reaction was carried out by preparing 50 µL of a reaction liquid comprising 0.1 µg of pHSG398 (manufactured by Takara Bio Company) as the template, 0.5 µmol/L of each of a synthetic DNA comprising the sequence of SEQ ID NO:3 and a synthetic DNA comprising the sequence of SEQ ID NO:4 as primers, 2.5 units of Pyrobest DNA polymerase (manufactured by Takara Bio), 5 µL of ×10 buffer solution for Pyrobest DNA polymerase (manufactured by Takara Bio), and 200 µmol/L of each dNTP (dATP, dGTP, dCTP and dTTP), and repeating the step of treatment at 96° C. for 15 seconds, at 55° C. for 30 seconds, and at 72° C. for 1 minute 30 times. The amplified DNA fragment was purified by a conventional method, after which the fragment was digested with the restriction enzymes BamHI and SalI; the DNA fragments was separated by agarose electrophoresis, after which the separated fragment was purified using the Wizard SV Gel and PCR Clean-Up System (manufactured by Promega Company) (hereinafter, abbreviated as DNA fragment purification kit) to yield a chloramphenicol resistance gene fragment.

Furthermore, a PCR reaction was carried out in the same manner with pMOB3 (derived from ATCC77282) as the template, using a synthetic DNA comprising the sequence of SEQ ID NO:5 and a synthetic DNA comprising the sequence of SEQ ID NO:6 as primers; the fragment was purified by a conventional method. The DNA fragment obtained was digested with the restriction enzymes SphI and SalI, after which the fragment was purified using agarose electrophoresis and a DNA purification kit to yield a levansucrase gene fragment. pHSG298 (manufactured by Takara Bio Company) was digested with the restriction enzymes BamHI and SphI and purified using agarose electrophoresis and a DNA fragment purification kit. The above-described three DNA fragments were ligated using the DNA Ligation Kit Ver.2.1 (manufactured by Takara Bio Company); competent cells of *Escherichia coli* DH5a (manufactured by TOYOBO Company) were transformed with the ligation products, and a transformant was selected with chloramphenicol resistance as the index. By extracting the plasmid from a colony of the selected transformant according to a publicly known method, and analyzing the structure thereof using restriction enzymes, acquirement of pHSGcatsacB comprising the chloramphenicol resistance gene (cat) and the levansucrase gene (sacB) was confirmed. A PCR reaction was carried out with the plasmid obtained as the template, using a synthetic DNA comprising the sequence of SEQ ID NO:7 and a synthetic DNA comprising the sequence of SEQ ID NO:8 as primers; the fragment was purified using a DNA fragment purification kit to yield a DNA fragment comprising the chloramphenicol resistance gene (cat) and the levansucrase gene (sacB) (hereinafter, abbreviated as cat-sacB cassette).

(2) Preparation of DNA Fragment for Deletion of aspC and DNA Fragment for Removal of Marker Inserted into aspC Region Each DNA fragment was prepared as described below.

A PCR reaction was carried out by preparing 50 µL of a reaction liquid comprising 0.1 µg of the *Escherichia coli* MG1655 strain genome DNA (ATCC700926D-5) as the template, 0.5 µmol/L of each of a synthetic DNA comprising the sequence of SEQ ID NO:9 and a synthetic DNA comprising the sequence of SEQ ID NO:11 as primers, 2.5 units of LA Tag DNA polymerase (manufactured by Takara Bio), 5 µL of ×10 buffer solution for LA Tag DNA polymerase (manufactured by Takara Bio), and 400 µmol/L of each dNTP (dATP, dGTP, dCTP and dTTP), and repeating the step of treatment at 94° C. for 1 minute, at 55° C. for 30 seconds, and at 72° C. for 7 minutes 30 times, to amplify a DNA fragment comprising aspC. Each of the 5' region of the aspC gene and the 3' region was amplified by a PCR reaction with the DNA fragment obtained as the template, using a synthetic DNA comprising the sequence of SEQ ID NO:9 and a synthetic DNA comprising the sequence of SEQ ID NO:13 as primers for 5' region, and using a synthetic DNA comprising the sequence of SEQ ID NO:11 and a synthetic DNA comprising the sequence of SEQ ID NO:14 as primers for 3' region, respectively; each DNA fragment obtained was purified using a DNA fragment purification kit; the DNA fragment obtained was purified using a DNA fragment purification kit.

Next, these two fragments and the cat-sacB cassette obtained in (1) above were mixed together, and a PCR reaction was carried out with this mixture as the template, using a synthetic DNA comprising the sequence of SEQ ID NO:10 and a synthetic DNA comprising the sequence of SEQ ID NO:12 as primers, to join the three fragments and amplify them. The DNA fragment obtained by this operation has a structure wherein the chloramphenicol resistance gene and the levansucrase gene are inserted between the 5'-end sequence and 3'-end sequence of the aspC gene. This DNA fragment was used as the DNA fragment for deletion of aspC.

Furthermore, each of the 5' region of the aspC gene and the 3' region was amplified by a PCR reaction with the DNA fragment comprising the aspC gene, amplified by the PCR reaction using a synthetic DNA comprising the sequence of SEQ ID NO:9 and the synthetic DNA comprising the sequence of SEQ ID NO:11 as primers, as the template, using a synthetic DNA comprising the sequence of SEQ ID NO:9 and a synthetic DNA comprising the sequence of SEQ ID NO:16 as primers for 5' region, and using a synthetic DNA having the sequence of SEQ ID NO:11 and a synthetic DNA comprising the sequence of SEQ ID NO:15 as primers for 3' region, respectively; each DNA fragment obtained was purified using a DNA fragment purification kit.

Next, these two fragments were mixed together, and a PCR reaction was carried out with this mixture as the template, using a synthetic DNA comprising the sequence of SEQ ID NO:10 and a synthetic DNA comprising the sequence of SEQ ID NO:12 as primers, to join the two fragments and amplify them. The DNA fragment obtained by this operation has a structure wherein the 5' region and 3' region of the aspC gene are directly joined together, and the aspC gene that encodes for the aspartate aminotransferase is largely deleted. This DNA fragment was used as the DNA fragment for removal of the marker inserted into the aspC region.

(3) Introduction of aspC Deletion Mutation into the BW25113 Strain by the Gene Replacement Method The DNA fragment for deletion of aspC obtained in (2) above was introduced into *Escherichia coli* BW25113/pKD46 (available as CGSC#7739 from The Coli Genetic Stock Center at Yale University) according to the method of Datsenko et al. [Proc. Natl. Acad. Sci. USA, 97,6640 (2000)] to cause homologous recombination with the chromosome DNA. Transformants were selected with chloramphenicol resistance as the index; colonies emerged were collected, and strains that did not grow on LB agar medium [a medium comprising 10 g of Tryptone (manufactured by Difco Company), 5 g of sodium chloride, 5 g of yeast extract (manufactured by Difco Company), and 20 g of Bactoagar (manufactured by Difco Company) in 1 L of water, adjusted to pH 7.2] containing 60 g/L sucrose were selected, after which the DNA fragment for removal of the marker inserted into the aspC region was introduced in the same way. A strain that had become non-sucrose-sensitive and chloramphenicol-sensitive was selected to obtain a strain successfully deprived of the cat-sacB cassette, namely the BWC/pKD46 strain. For confirmation, the chromosome DNA of the strain obtained was extracted by a publicly known method, and a PCR reaction was carried out with this as the template, using a synthetic DNA comprising the sequence of SEQ ID NO:10 and a synthetic DNA comprising the sequence of SEQ ID NO:12 as primers; a DNA fragment with the same length as that of the DNA fragment for removal of the marker was amplified.

EXAMPLE 2

L-Glutamic Acid Production Experiment with the BW25113 Strain and the aspC Deletion Mutation Strain The aspC-deficient BWC/pKD46 strain obtained in Example 1 was deprived of the pKD46 plasmid to obtain the BWC strain. Specifically, the aspC-deficient BWC/pKD46 strain was inoculated to a test tube containing 8 mL of LB liquid medium and subjected to shaking culture at 42° C. overnight; the cultured broth obtained was streaked over LB agar medium [a medium containing 10 g of Tryptone (manufactured by Difco Company), 5 g of sodium chloride, 5 g of yeast extract (manufactured by Difco Company), and 20 g of Bactoagar (manufactured by Difco Company) in 1 L of water, adjusted to pH 7.2]; from the colonies emerged, a strain that became no longer able to grow on an LB agar medium containing 100 mg/L ampicillin was selected.

The aspC mutant BWC strain and the parent BW25113 strain (CGSC#7736) were cultured on LB agar medium at 30° C. for 24 hours, after which each was inoculated to a conical flask containing 350 mL of LB liquid medium [a medium containing 10 g of Tryptone (manufactured by Difco Company), 5 g of sodium chloride, and 5 g of yeast extract (manufactured by Difco Company) in 1 L of water, adjusted to pH 7.2] and cultured at 30° C. for 16 hours.

20 mL of the seed cultured broth obtained was inoculated to a jar fermenter containing 780 mL of main culture medium [containing 45 g of glucose, 10 g/L yeast extract powder (AY-80; manufactured by Asahi Food & Healthcare Company), 10 g of ammonium sulfate, 2 g/L sodium chloride, 1.0 g of dipotassium hydrogen phosphate, 0.5 g of magnesium sulfate heptahydrate, 278 mg of ferrous sulfate heptahydrate, 10 mg of manganese sulfate pentahydrate, and 8 mg of thiamine hydrochloride in 1 L of water, sterilized and then adjusted to pH 7.0 with sulfuric acid] and cultured at a stirring rotation rate of 800 rpm, with aeration of 1 L per minute, at 30° C. for 16 hours.

Cell bodies were removed from the cultured broth via centrifugation; the amount of L-amino acid accumulated in the supernatant was quantified by high performance liquid chromatography (HPLC) according to the method of Bank et al. [Anal. Biochem., 240,167 (1996)].

The results are shown in Table 1.

TABLE 1

| Strain | Glu (g/L) |
|---|---|
| BW25113 | 0.77 |
| BWC | 3.60 |

In the BWC strain deprived of the gene aspC that encodes for the aspartate aminotransferase, the amount of L-glutamic acid (Glu) produced evidently improved compared with the parent strain BW25113 strain.

EXAMPLE 3

Establishment of a Proline-Producing Strain and the Same Strain but Lacking the Aspartate Aminotransferase Gene (1) Preparation of DNA Fragment for Deletion of Proline Degrading Enzyme Gene putA, DNA Fragment for Removal of Marker Inserted into putA Region, DNA Fragment for Deletion of proB, and DNA Fragment for Introduction of proB74 Mutation Each DNA fragment was prepared as described below.

A PCR reaction was carried out with the *Escherichia coli* MG1655 strain genome DNA as the template, using a synthetic DNA comprising the sequence of SEQ ID NO:17 and a synthetic DNA comprising the sequence of SEQ ID NO:19 as primers, to amplify a DNA fragment comprising putA. Each of the 5' region of putA and the 3' region of putA was amplified by a PCR reaction with the DNA fragment obtained as the template, using a synthetic DNA comprising the sequence of SEQ ID NO:17 and a synthetic DNA comprising the sequence of SEQ ID NO:21 for 5' region, and using a synthetic DNA comprising the sequence of SEQ ID NO:19 and a synthetic DNA comprising the sequence of SEQ ID NO:22 for 3' region, respectively; each DNA fragment obtained was purified using a DNA fragment purification kit. Next, these two fragments and the cat-sacB cassette obtained in Example 1(1) were mixed, and a PCR reaction was carried out with this mixture as the template, using a synthetic DNA comprising the sequence of SEQ ID NO:18 and a synthetic DNA comprising the sequence of SEQ ID NO:20 as primers, to join the three fragments and amplify them. The DNA fragment obtained by this operation has a structure wherein the chloramphenicol resistance gene and the levansucrase gene are inserted between the 5'-end sequence and 3'-end sequence of the putA gene. This DNA fragment was used as the DNA fragment for deletion of putA.

Furthermore, each of the 5' region of the putA gene and the 3' region was amplified by a PCR reaction with the DNA fragment comprising the putA gene, amplified by the PCR reaction using a synthetic DNA comprising the sequence of SEQ ID NO:17 and a synthetic DNA comprising the sequence of SEQ ID NO:19 as primers, as the template, using a synthetic DNA comprising the sequence of SEQ ID NO:17 and a synthetic DNA comprising the sequence of SEQ ID NO:24 as primers for 5' region, and using a synthetic DNA comprising the sequence of SEQ ID NO:19 and a synthetic DNA comprising the sequence of SEQ ID NO:23 as primers for 3' region, respectively; each DNA fragment obtained was purified using a DNA fragment purification kit. Next, these two fragments were mixed together, and a PCR reaction was carried out with this mixture as the template, using a synthetic DNA comprising the sequence of SEQ ID NO:18 and a synthetic DNA comprising the sequence of SEQ ID NO:20 as primers, to join the two fragments and amplify them. The DNA fragment obtained by this operation has a structure wherein the 5' region and 3' region of the putA gene are directly joined together, and the putA gene is largely deleted. This DNA fragment was used as the DNA fragment for removal of the marker inserted into the putA region.

Next, a PCR reaction was carried out with the *Escherichia coli* MG1655 strain genome DNA as the template, using a synthetic DNA comprising the sequence of SEQ ID NO:25 and a synthetic DNA comprising the sequence of SEQ ID NO:27 as primers, to amplify a DNA fragment comprising proB. Each of the 5" region of proB and the 3' region of proB was amplified by a PCR reaction with the DNA fragment obtained as the template, using a synthetic DNA comprising the sequence of SEQ ID NO:25 and a synthetic DNA comprising the sequence of SEQ ID NO:29 for 5' region, and using a synthetic DNA comprising the sequence of SEQ ID NO:27 and a synthetic DNA comprising the sequence of SEQ ID NO:30 for 3' region, respectively; each DNA fragment obtained was purified using a DNA fragment purification kit. Next, these two fragments and the cat-sacB cassette obtained in Example 1(1) were mixed together, and a PCR reaction was carried out with this mixture as the template, using a synthetic DNA comprising the sequence of SEQ ID NO:26 and a synthetic DNA comprising the sequence of SEQ ID NO:28 as primers, to join the three fragments and amplify them. The DNA fragment obtained by this operation has a structure wherein the chloramphenicol resistance gene and the levansucrase gene are inserted between the 5'-end sequence and 3'-end sequence of the proB gene. This DNA fragment was used as the DNA fragment for deletion of proB.

Furthermore, each of the 5' region of the proB gene and the 3' region was amplified by a PCR reaction with the DNA fragment comprising the proB gene, amplified by the PCR reaction using synthetic DNAs of SEQ ID NO:25 and 27 as primers, as the template, using a synthetic DNA comprising the sequence of SEQ ID NO:25 and a synthetic DNA comprising the sequence of SEQ ID NO:32 as primers for 5' region, and using a synthetic DNA comprising the sequence of SEQ ID NO:27 and a synthetic DNA comprising the sequence of SEQ ID NO:31 as primers for 3' region, respectively; each DNA fragment obtained was purified using a DNA fragment purification kit. Next, these two fragments were mixed together, and a PCR reaction was carried out with this mixture as the template, using a synthetic DNA comprising the sequence of SEQ ID NO:26 and a synthetic DNA comprising the sequence of SEQ ID NO:28 as primers, to join the two fragments and amplify them. In the DNA fragment obtained by this operation, the 319th nucleotide of the proB gene was substituted from A to G. It was reported that feedback inhibition by proline was cancelled in the γ glutamyl kinase encoded by proB74 incorporating this mutation [Gene, 64,199 (1988)]. The DNA fragment obtained by this operation was used as the DNA fragment for introduction of proB74 mutation.

(2) Introduction of putA Deletion Mutation into the BW25113 Strain by the Gene Replacement Method BW25113/pKD46 was subjected to the same operation as Example 1(3), using the DNA fragment for deletion of the proline degrading enzyme gene putA and the DNA fragment for removal of the marker inserted into the putA region, to obtain the BWA/pKD46 strain.

(3) Introduction of aspC Deletion Mutation into the BWA Strain by the Gene Replacement Method The BWA/pKD46 strain was subjected to the same operation as Example 1 (3), using the DNA fragment for deletion of aspC and the DNA fragment for removal of the marker inserted into the aspC region, to obtain the BWAC/pKD46 strain.

(4) Introduction of proB74 Mutation by the Gene Replacement Method

The BWA/pKD46 strain and the BWAC/pKD46 strain were subjected to the same operation as Example 1(3), using the DNA fragment for deletion of proB, and the DNA fragment for introduction of the proB74 mutation, to obtain the BWAP/pKD46 strain and the BWACP/pKD46 strain, respectively.

EXAMPLE 4

L-Proline Production Experiment with the BWAP Strain and the BWACP Strain

The BWAP/pKD46 strain and aspC-deficient BWACP/pKD46 strain obtained in Example 3 were deprived of the pKD46 plasmid to obtain the BWAP strain and the BWACP strain, respectively. The BWAP strain and the BWACP strain were cultured on LB agar medium at 30° C. for 24 hours; each strain was inoculated to a test tube containing 8 mL of LB liquid medium and cultured at 30° C. for 16 hours.

0.4 mL of each seed cultured broth obtained was inoculated to a test tube containing 8 mL of main culture medium [containing 20 g of glucose, 4 g/L yeast extract powder (AY-80; manufactured by Asahi Food & Healthcare Company), 10 g of ammonium sulfate, 2 g/L sodium chloride, 1.0 g of dipotassium hydrogen phosphate, 0.5 g of magnesium sulfate heptahydrate, 278 mg of ferrous sulfate heptahydrate, and 25 g of calcium carbonate in 1 L of water, sterilized and then adjusted to pH 7.0 with sulfuric acid] and cultured at 30° C. for 30 hours.

Cell bodies were removed from the cultured broth via centrifugation; the amount of L-amino acid accumulated in the supernatant was quantified by high performance liquid chromatography (HPLC).

The results are shown in Table 2.

TABLE 2

| Strain | Pro (g/L) |
|--------|-----------|
| BWAP   | 1.18      |
| BWACP  | 2.70      |

In the BWACP strain deprived of aspC, the amount of L-proline (Pro) produced evidently improved compared with the BWAP strain.

EXAMPLE 5

Establishment of an Arginine-Producing Strain and the Same Strain but Lacking the Aspartate Aminotransferase Gene (1) Preparation of DNA Fragment for Deletion of the N-acetylglutamic Acid Synthase Gene argA, DNA Fragment for Introduction of argA215 Mutation, DNA Fragment for Deletion of argR, and DNA Fragment for Removal of Marker Inserted into argR Region A PCR reaction was carried out with the *Escherichia coli* MG1655 strain genome DNA as the template, using a synthetic DNA comprising the sequence of SEQ ID NO:33 and a synthetic DNA comprising the sequence of SEQ ID NO:35 as primers, to amplify a DNA fragment comprising argA. Each of the 5" region of argA and the 3' region of argA was amplified by a PCR reaction with the DNA fragment obtained as the template, using a synthetic DNA comprising the sequence of SEQ ID NO:33 and a synthetic DNA comprising the sequence of SEQ ID NO:37 for 5' region, and using a synthetic DNA comprising the sequence of SEQ ID NO:35 and a synthetic DNA comprising the sequence of SEQ ID NO:38, respectively; each DNA fragment obtained was purified using a DNA fragment purification kit. Next, these two fragments and the cat-sacB cassette obtained in Example 1(1) were mixed together, and a PCR reaction was carried out with this mixture as the template, using a synthetic DNA comprising the sequence of SEQ ID NO:34 and a synthetic DNA comprising the sequence of SEQ ID NO:36 as primers, to join the three fragments and amplify them. The DNA fragment obtained by this operation has a structure wherein the chloramphenicol resistance gene and the levansucrase gene are inserted between the 5'-end sequence and 3'-end sequence of the argA gene. This DNA fragment was used as the DNA fragment for destruction of argA.

Furthermore, each of the 5' region of the argA gene and the 3' region was amplified by a PCR reaction with the DNA fragment comprising the argA gene, amplified by the PCR reaction using a synthetic DNA comprising the sequence of SEQ ID NO:33 and a synthetic DNA comprising the sequence of SEQ ID NO:35 as primers, as the template, using a synthetic DNA comprising the sequence of SEQ ID NO:33 and a synthetic DNA comprising the sequence of SEQ ID NO:40 as primers for 5' region, and using a synthetic DNA comprising the sequence of SEQ ID NO:35 and a synthetic DNA comprising the sequence of SEQ ID NO:39 as primers for 3' region, respectively; each DNA fragment obtained was purified using a DNA fragment purification kit.

Next, these two fragments were mixed together, and a PCR reaction was carried out with this mixture as the template, using a synthetic DNA comprising the sequence of SEQ ID NO:34 and a synthetic DNA comprising the sequence of SEQ ID NO:36 as primers, to join the two fragments and amplify them. In the DNA fragment obtained by this operation, the 56th nucleotide of the argA gene was substituted from A to G. It was reported that feedback inhibition by arginine was cancelled in the N-acetylglutamic acid synthetase encoded by argA215 incorporating this mutation [Appl. Environ. Microbiol., 64, 1805 (1998)]. The DNA fragment obtained by this operation was used as the DNA fragment for introduction of argA215 mutation.

Next, a PCR reaction was carried out with the *Escherichia coli* MG1655 strain genome DNA as the template, using a synthetic DNA having the sequence of SEQ ID NO:41 and a synthetic DNA having the sequence of SEQ ID NO:43 as primers, to amplify a DNA fragment comprising argR. Each of the 5' region of argR and the 3' region of argR was amplified by a PCR reaction with the DNA fragment obtained as the template, using a synthetic DNA comprising the sequence of SEQ ID NO:41 and a synthetic DNA comprising the sequence of SEQ ID NO:45 for 5' region, and using a synthetic DNA comprising the sequence of SEQ ID NO:43 and a synthetic DNA comprising the sequence of SEQ ID NO:46, respectively; each DNA fragment obtained was purified using a DNA fragment purification kit. Next, these two fragments and the cat-sacB cassette obtained in Example 1 (1) were mixed together, and a PCR reaction was carried out with this mixture as the template, using a synthetic DNA comprising the sequence of SEQ ID NO:42 and a synthetic DNA comprising the sequence of SEQ ID NO:44 as primers, to join the three fragments and amplify them. The DNA fragment obtained by this operation has a structure wherein the chloramphenicol resistance gene and the levansucrase gene are inserted between the 5'-end sequence and 3'-end sequence of the argR gene. This DNA fragment was used as the DNA fragment for destruction of argR.

Furthermore, each of the 5' region of the argR gene and the 3' region was amplified by a PCR reaction with the DNA fragment comprising the argR gene, amplified by the PCR reaction using a synthetic DNA comprising the sequence of SEQ ID NO:41 and a synthetic DNA comprising the sequence of SEQ ID NO:43 as primers, as the template, using a synthetic DNA comprising the sequence of SEQ ID NO:41 and a synthetic DNA comprising the sequence of SEQ ID NO:48 as primers for 5' region, and using a synthetic DNA comprising the sequence of SEQ ID NO:43 and a synthetic DNA comprising the sequence of SEQ ID NO:47 as primers for 3' region, respectively; each DNA fragment obtained was purified using a DNA fragment purification kit. Next, these two fragments were mixed together, and a PCR reaction was carried out with this mixture as the template, using a synthetic DNA comprising the sequence of SEQ ID NO:42 and a synthetic DNA comprising the sequence of SEQ ID NO:44 as primers, to join the two fragments and amplify them. The DNA fragment obtained by this operation has a structure wherein the 5' region and 3' region of the argR gene are directly joined together, and the argR gene is largely deleted. This DNA fragment was used as the DNA fragment for removal of the marker inserted into the argR region.

(2) Introduction of argA215 Mutation into the BW25113 Strain by the Gene Replacement Method The BW25113/pKD46 strain was subjected to the same operation as Example 1 (3) using the DNA fragment for deletion of the N-acetylglutamic acid synthase gene argA and the DNA fragment for introduction of argA215 mutation, to obtain the desired strain.

(3) Introduction of argR Deletion Mutation by the Gene Replacement Method

The strain obtained in (2) above was subjected to the same operation as Example 1 (3) using the DNA fragment for deletion of argR and the DNA fragment for removal of the marker inserted into the argR region, to obtain the BWR/pKD46 strain.

(4) Introduction of aspC Deletion Mutation into the BWR Strain by the Gene Replacement Method The BWR strain was subjected to the same operation as Example 1(3) using the DNA fragment for deletion of aspC and the DNA fragment for removal of the marker inserted into the aspC region, to obtain the desired BWRC/pKD46 strain.

EXAMPLE 6

L-Arginine, L-Citrulline, and L-Ornithine Production Experiments with the BWR Strain and the Same Strain but Lacking aspC The BWR/pKD46 strain and aspC-deficient BWRC/pKD46 strain obtained in Example 5 were deprived of the pKD46 plasmid to yield the BWR strain and the BWRC strain. Amino acid production experiments with the BWR and BWRC strains were performed in the same manner as Example 4.

The results are shown in Table 3.

TABLE 3

| Strain | Arg (g/L) | Cit (g/L) | Orn (g/L) |
|---|---|---|---|
| BWR | 1.94 | n.d. | n.d. |
| BWRC | 2.36 | 2.96 | 0.12 |

In the BWRC strain deprived of aspC, the amount of L-arginine (Arg) produced evidently improved compared with the parent BWR strain. For L-citrulline (Cit) and L-ornithine (Orn) as well, the BWRC strain exhibited higher productivity than the parent BWR strain.

EXAMPLE 7

Establishment of a Hydroxyproline-Producing Strain and the Same Strain but Lacking the Aspartate Aminotransferase Gene The BWA/pKD46 strain and BWAC/pKD46 strain prepared in Example 3(2) and (3) were deprived of the pKD46 plasmid to yield the BWA strain and the BWAC strain, after which the plasmid pWFP1 described in the literature [J. Biosci. Bioeng., 90, 522 (2000)] was introduced according to the method of Dower et al. [Nucleic Acids Research, 16,6127 (1988)] by electroporation to obtain respective transformants with ampicillin resistance as the marker.

EXAMPLE 8

L-proline and L-hydroxyproline Production Experiments with the BWA/pWFP1 Strain and the Same Strain but Lacking aspC, Namely the BWAC/pWFP1 Strain Amino acid production experiments of the BWA/pWFP1 and BWAC/pWFP1 strains prepared in Example 7 were performed in the same manner as Example 4.

The results are shown in Table 4.

TABLE 4

| Strain | Pro (g/L) | Hyp (g/L) |
|---|---|---|
| BWA/pWFP1 | 1.91 | 1.30 |
| BWAC/pWFP1 | 2.62 | 2.11 |

In the aspC-deficient BWAC/pWFP1 strain, the amounts of L-proline (Pro) and L-hydroxyproline (Hyp) produced evidently improved compared with the BWA/pWFP1 strain.

INDUSTRIAL APPLICABILITY

The present invention enables to efficiently produce L-amino acids using microorganisms with improved L-amino acid production efficiency compared with conventional microorganisms, making it possible to efficiently provide L-amino acids that find a wide variety of use applications in the fields of pharmaceuticals, health foods and the like.

This application is based on a patent application No. 2009-028693 filed in Japan (filing date: Feb. 10, 2009), the contents of which are incorporated in full herein.

[Sequence Listing Free Text]
SEQ ID NO:3—explanation of artificial sequence: synthetic DNA
SEQ ID NO:4—explanation of artificial sequence: synthetic DNA
SEQ ID NO:5—explanation of artificial sequence: synthetic DNA
SEQ ID NO:6—explanation of artificial sequence: synthetic DNA
SEQ ID NO:7—explanation of artificial sequence: synthetic DNA
SEQ ID NO:8—explanation of artificial sequence: synthetic DNA
SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:17—explanation of artificial sequence: synthetic DNA
SEQ ID NO:18—explanation of artificial sequence: synthetic DNA
SEQ ID NO:19—explanation of artificial sequence: synthetic DNA
SEQ ID NO:20—explanation of artificial sequence: synthetic DNA
SEQ ID NO:21—explanation of artificial sequence: synthetic DNA
SEQ ID NO:22—explanation of artificial sequence: synthetic DNA
SEQ ID NO:23—explanation of artificial sequence: synthetic DNA
SEQ ID NO:24—explanation of artificial sequence: synthetic DNA
SEQ ID NO:25—explanation of artificial sequence: synthetic DNA
SEQ ID NO:26—explanation of artificial sequence: synthetic DNA
SEQ ID NO:27—explanation of artificial sequence: synthetic DNA
SEQ ID NO:28—explanation of artificial sequence: synthetic DNA
SEQ ID NO:29—explanation of artificial sequence: synthetic DNA
SEQ ID NO:30—explanation of artificial sequence: synthetic DNA
SEQ ID NO:31—explanation of artificial sequence: synthetic DNA
SEQ ID NO:32—explanation of artificial sequence: synthetic DNA
SEQ ID NO:33—explanation of artificial sequence: synthetic DNA
SEQ ID NO:34—explanation of artificial sequence: synthetic DNA
SEQ ID NO:35—explanation of artificial sequence: synthetic DNA SEQ ID NO:36—explanation of artificial sequence: synthetic DNA
SEQ ID NO:37—explanation of artificial sequence: synthetic DNA
SEQ ID NO:38—explanation of artificial sequence: synthetic DNA
SEQ ID NO:39—explanation of artificial sequence: synthetic DNA
SEQ ID NO:40—explanation of artificial sequence: synthetic DNA
SEQ ID NO:41—explanation of artificial sequence: synthetic DNA
SEQ ID NO:42—explanation of artificial sequence: synthetic DNA
SEQ ID NO:43—explanation of artificial sequence: synthetic DNA
SEQ ID NO:44—explanation of artificial sequence: synthetic DNA
SEQ ID NO:45—explanation of artificial sequence: synthetic DNA
SEQ ID NO:46—explanation of artificial sequence: synthetic DNA
SEQ ID NO:47—explanation of artificial sequence: synthetic DNA
SEQ ID NO:48—explanation of artificial sequence: synthetic DNA

The invention claimed is:

1. A process for producing an L-amino acid which comprises:

culturing in a medium a mutant *Escherichia coli* (*E. coli*) microorganism, wherein the mutant *E. coli* microorganism comprises a substitution, deletion, or addition of one or more bases in a gene encoding aspartate aminotransferase as compared to the gene encoding aspartate aminotransferase in a parental *E. coli* microorganism, and wherein aspartate aminotransferase activity of the mutant *E. coli* microorganism is absent as compared to the aspartate aminotransferase activity of the parental microorganism, producing and accumulating the L-amino acid in the medium, wherein the mutant *E. coli* microorganism produces a greater amount of the L-amino acid than the parental *E. coli* microorganism under the same culture conditions, and collecting the L-amino acid from the medium, wherein the L-amino acid is selected from L-glutamine, L-proline, L-ornithine, L-citrulline, L-arginine, and L-hydroxyproline, wherein the aspartate aminotransferase in the parental *E. coli* microorganism is a protein consisting of the amino acid sequence shown in SEQ ID NO: 2.

2. The process of claim 1, wherein the aspartate aminotransferase in the parental *E. coli* microorganism is encoded by a DNA consisting of the nucleotide sequence shown in SEQ ID NO: 1.

* * * * *

```
                         SEQUENCE LISTING

<160> NUMBER OF SEQ ID NOS: 48

<210> SEQ ID NO 1
<211> LENGTH: 1191
<212> TYPE: DNA
<213> ORGANISM: Escherichia coli
<220> FEATURE:
<221> NAME/KEY: CDS
<222> LOCATION: (1)..(1191)

<400> SEQUENCE: 1 atg ttt gag aac att acc gcc gct cct gcc gac ccg att ctg ggc ctg      48
Met Phe Glu Asn Ile Thr Ala Ala Pro Ala Asp Pro Ile Leu Gly Leu
1               5                   10                  15 gcc gat ctg ttt cgt gcc gat gaa cgt ccc ggc aaa att aac ctc ggg      96
Ala Asp Leu Phe Arg Ala Asp Glu Arg Pro Gly Lys Ile Asn Leu Gly
                20                  25                  30 att ggt gtc tat aaa gat gag acg ggc aaa acc ccg gta ctg acc agc     144
Ile Gly Val Tyr Lys Asp Glu Thr Gly Lys Thr Pro Val Leu Thr Ser
            35                  40                  45 gtg aaa aag gct gaa cag tat ctg ctc gaa aat gaa acc acc aaa aat     192
Val Lys Lys Ala Glu Gln Tyr Leu Leu Glu Asn Glu Thr Thr Lys Asn
        50                  55                  60 tac ctc ggc att gac ggc atc cct gaa ttt ggt cgc tgc act cag gaa     240
Tyr Leu Gly Ile Asp Gly Ile Pro Glu Phe Gly Arg Cys Thr Gln Glu
65                  70                  75                  80 ctg ctg ttt ggt aaa ggt agc gcc ctg atc aat gac aaa cgt gct cgc     288
Leu Leu Phe Gly Lys Gly Ser Ala Leu Ile Asn Asp Lys Arg Ala Arg
                85                  90                  95 acg gca cag act ccg ggg ggc act ggc gca cta cgc gtg gct gcc gat     336
Thr Ala Gln Thr Pro Gly Gly Thr Gly Ala Leu Arg Val Ala Ala Asp
                100                 105                 110 ttc ctg gca aaa aat acc agc gtt aag cgt gtg tgg gtg agc aac cca     384
Phe Leu Ala Lys Asn Thr Ser Val Lys Arg Val Trp Val Ser Asn Pro
            115                 120                 125 agc tgg ccg aac cat aag agc gtc ttt aac tct gca ggt ctg gaa gtt     432
Ser Trp Pro Asn His Lys Ser Val Phe Asn Ser Ala Gly Leu Glu Val
        130                 135                 140 cgt gaa tac gct tat tat gat gcg gaa aat cac act ctt gac ttc gat     480
Arg Glu Tyr Ala Tyr Tyr Asp Ala Glu Asn His Thr Leu Asp Phe Asp
145                 150                 155                 160 gca ctg att aac agc ctg aat gaa gct cag gct ggc gac gta gtg ctg     528
Ala Leu Ile Asn Ser Leu Asn Glu Ala Gln Ala Gly Asp Val Val Leu
                165                 170                 175 ttc cat ggc tgc tgc cat aac cca acc ggt atc gac cct acg ctg gaa     576
Phe His Gly Cys Cys His Asn Pro Thr Gly Ile Asp Pro Thr Leu Glu
            180                 185                 190
```

```
caa tgg caa aca ctg gca caa ctc tcc gtt gag aaa ggc tgg tta ccg      624
Gln Trp Gln Thr Leu Ala Gln Leu Ser Val Glu Lys Gly Trp Leu Pro
        195                 200                 205 ctg ttt gac ttc gct tac cag ggt ttt gcc cgt ggt ctg gaa gaa gat      672
Leu Phe Asp Phe Ala Tyr Gln Gly Phe Ala Arg Gly Leu Glu Glu Asp
    210                 215                 220 gct gaa gga ctg cgc gct ttc gcg gct atg cat aaa gag ctg att gtt      720
Ala Glu Gly Leu Arg Ala Phe Ala Ala Met His Lys Glu Leu Ile Val
225                 230                 235                 240 gcc agt tcc tac tct aaa aac ttt ggc ctg tac aac gag cgt gtt ggc      768
Ala Ser Ser Tyr Ser Lys Asn Phe Gly Leu Tyr Asn Glu Arg Val Gly
                245                 250                 255 gct tgt act ctg gtt gct gcc gac agt gaa acc gtt gat cgc gca ttc      816
Ala Cys Thr Leu Val Ala Ala Asp Ser Glu Thr Val Asp Arg Ala Phe
            260                 265                 270 agc caa atg aaa gcg gcg att cgc gct aac tac tct aac cca cca gca      864
Ser Gln Met Lys Ala Ala Ile Arg Ala Asn Tyr Ser Asn Pro Pro Ala
        275                 280                 285 cac ggc gct tct gtt gtt gcc acc atc ctg agc aac gat gcg tta cgt      912
His Gly Ala Ser Val Val Ala Thr Ile Leu Ser Asn Asp Ala Leu Arg
    290                 295                 300 gcg att tgg gaa caa gag ctg act gat atg cgc cag cgt att cag cgt      960
Ala Ile Trp Glu Gln Glu Leu Thr Asp Met Arg Gln Arg Ile Gln Arg
305                 310                 315                 320 atg cgt cag ttg ttc gtc aat acg ctg cag gaa aaa ggc gca aac cgc     1008
Met Arg Gln Leu Phe Val Asn Thr Leu Gln Glu Lys Gly Ala Asn Arg
                325                 330                 335 gac ttc agc ttt atc atc aaa cag aac ggc atg ttc tcc ttc agt ggc     1056
Asp Phe Ser Phe Ile Ile Lys Gln Asn Gly Met Phe Ser Phe Ser Gly
            340                 345                 350 ctg aca aaa gaa caa gtg ctg cgt ctg cgc gaa gag ttt ggc gta tat     1104
Leu Thr Lys Glu Gln Val Leu Arg Leu Arg Glu Glu Phe Gly Val Tyr
        355                 360                 365 gcg gtt gct tct ggt cgc gta aat gtg gcc ggg atg aca cca gat aac     1152
Ala Val Ala Ser Gly Arg Val Asn Val Ala Gly Met Thr Pro Asp Asn
    370                 375                 380 atg gct ccg ctg tgc gaa gcg att gtg gca gtg ctg taa                 1191
Met Ala Pro Leu Cys Glu Ala Ile Val Ala Val Leu
385                 390                 395

<210> SEQ ID NO 2
<211> LENGTH: 396
<212> TYPE: PRT
<213> ORGANISM: Escherichia coli

<400> SEQUENCE: 2

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45

Val Lys Lys Ala Glu Gln Tyr Leu Leu Glu Asn Glu Thr Thr Lys Asn
    50                  55                  60

Tyr Leu Gly Ile Asp Gly Ile Pro Glu Phe Gly Arg Cys Thr Gln Glu
65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
```

-continued

```
                    100                 105                 110
    Phe Leu Ala Lys Asn Thr Ser Val Lys Arg Val Trp Val Ser Asn Pro
            115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
    145                 150                 155                 160

Ala Leu Ile Asn Ser Leu Asn Glu Ala Gln Ala Gly Asp Val Val Leu
                    165                 170                 175

Phe His Gly Cys Cys His Asn Pro Thr Gly Ile Asp Pro Thr Leu Glu
                    180                 185                 190

Gln Trp Gln Thr Leu Ala Gln Leu Ser Val Glu Lys Gly Trp Leu Pro
                    195                 200                 205

Leu Phe Asp Phe Ala Tyr Gln Gly Phe Ala Arg Gly Leu Glu Glu Asp
            210                 215                 220

Ala Glu Gly Leu Arg Ala Phe Ala Ala Met His Lys Glu Leu Ile Val
    225                 230                 235                 240

Ala Ser Ser Tyr Ser Lys Asn Phe Gly Leu Tyr Asn Glu Arg Val Gly
                    245                 250                 255

Ala Cys Thr Leu Val Ala Ala Asp Ser Glu Thr Val Asp Arg Ala Phe
                    260                 265                 270

Ser Gln Met Lys Ala Ala Ile Arg Ala Asn Tyr Ser Asn Pro Pro Ala
                    275                 280                 285

His Gly Ala Ser Val Val Ala Thr Ile Leu Ser Asn Asp Ala Leu Arg
            290                 295                 300

Ala Ile Trp Glu Gln Glu Leu Thr Asp Met Arg Gln Arg Ile Gln Arg
    305                 310                 315                 320

Met Arg Gln Leu Phe Val Asn Thr Leu Gln Lys Gly Ala Asn Arg
                    325                 330                 335

Asp Phe Ser Phe Ile Ile Lys Gln Asn Gly Met Phe Ser Phe Ser Gly
                    340                 345                 350

Leu Thr Lys Glu Gln Val Leu Arg Leu Arg Glu Glu Phe Gly Val Tyr
                    355                 360                 365

Ala Val Ala Ser Gly Arg Val Asn Val Ala Gly Met Thr Pro Asp Asn
            370                 375                 380

Met Ala Pro Leu Cys Glu Ala Ile Val Ala Val Leu
    385                 390                 395

<210> SEQ ID NO 3
<211> LENGTH: 42
<212> TYPE: DNA
<213> ORGANISM: Artificial Sequence
<220> FEATURE:
<223> OTHER INFORMATION: synthetic DNA

<400> SEQUENCE: 3
aatcgggatc cgcggccgca gaggcggttt gcgtattgga gc                          42

<210> SEQ ID NO 4
<211> LENGTH: 51
<212> TYPE: DNA
<213> ORGANISM: Artificial Sequence
<220> FEATURE:
<223> OTHER INFORMATION: synthetic DNA

<400> SEQUENCE: 4
ggatttgact acgggcctaa agtcgacaga ataaataaat cctggtgtcc c                51
```

<210> SEQ ID NO 5
<211> LENGTH: 42
<212> TYPE: DNA
<213> ORGANISM: Artificial Sequence
<220> FEATURE:
<223> OTHER INFORMATION: synthetic DNA

<400> SEQUENCE: 5
acggagcatg cgcggccgct caaaatcggt ggagctgcat ga                    42

<210> SEQ ID NO 6
<211> LENGTH: 54
<212> TYPE: DNA
<213> ORGANISM: Artificial Sequence
<220> FEATURE:
<223> OTHER INFORMATION: synthetic DNA

<400> SEQUENCE: 6
gggacaccag gatttattta ttctgtcgac tttaggcccg tagtctgcaa atcc        54

<210> SEQ ID NO 7
<211> LENGTH: 29
<212> TYPE: DNA
<213> ORGANISM: Artificial Sequence
<220> FEATURE:
<223> OTHER INFORMATION: synthetic DNA

<400> SEQUENCE: 7
gcggccgcat atcggcattt tcttttgcg                                   29

<210> SEQ ID NO 8
<211> LENGTH: 27
<212> TYPE: DNA
<213> ORGANISM: Artificial Sequence
<220> FEATURE:
<223> OTHER INFORMATION: synthetic DNA

<400> SEQUENCE: 8
gcggccgcac ttattcaggc gtagcac                                     27

<210> SEQ ID NO 9
<211> LENGTH: 30
<212> TYPE: DNA
<213> ORGANISM: Artificial Sequence
<220> FEATURE:
<223> OTHER INFORMATION: synthetic DNA

<400> SEQUENCE: 9
gcactttcac ggtagcgaaa cgttagtttg                                  30

<210> SEQ ID NO 10
<211> LENGTH: 31
<212> TYPE: DNA
<213> ORGANISM: Artificial Sequence
<220> FEATURE:
<223> OTHER INFORMATION: synthetic DNA

<400> SEQUENCE: 10
ggcaacaaag tagatctgta cggtaaagct g                                31

<210> SEQ ID NO 11
<211> LENGTH: 31
<212> TYPE: DNA
<213> ORGANISM: Artificial Sequence
<220> FEATURE:

<223> OTHER INFORMATION: synthetic DNA

<400> SEQUENCE: 11
ccagaagtgc atataaacga taacattgac c                                    31

<210> SEQ ID NO 12
<211> LENGTH: 31
<212> TYPE: DNA
<213> ORGANISM: Artificial Sequence
<220> FEATURE:
<223> OTHER INFORMATION: synthetic DNA

<400> SEQUENCE: 12
gcgcgaacaa aataaagtcc atcgacccag g                                    31

<210> SEQ ID NO 13
<211> LENGTH: 50
<212> TYPE: DNA
<213> ORGANISM: Artificial Sequence
<220> FEATURE:
<223> OTHER INFORMATION: synthetic DNA

<400> SEQUENCE: 13
gaaaatgccg atatgcggcc gccaactatt actgatgaaa acgcaggctg                50

<210> SEQ ID NO 14
<211> LENGTH: 50
<212> TYPE: DNA
<213> ORGANISM: Artificial Sequence
<220> FEATURE:
<223> OTHER INFORMATION: synthetic DNA

<400> SEQUENCE: 14
cgcctgaata agtgcggccg caggaaaaag gcgcaaaccg cgacttcagc                50

<210> SEQ ID NO 15
<211> LENGTH: 45
<212> TYPE: DNA
<213> ORGANISM: Artificial Sequence
<220> FEATURE:
<223> OTHER INFORMATION: synthetic DNA

<400> SEQUENCE: 15
catcagtaat agttggagga aaaggcgca aaccgcgact tcagc                      45

<210> SEQ ID NO 16
<211> LENGTH: 46
<212> TYPE: DNA
<213> ORGANISM: Artificial Sequence
<220> FEATURE:
<223> OTHER INFORMATION: synthetic DNA

<400> SEQUENCE: 16
gtttgcgcct ttttcctcca actattactg atgaaaacgc aggctg                    46

<210> SEQ ID NO 17
<211> LENGTH: 31
<212> TYPE: DNA
<213> ORGANISM: Artificial Sequence
<220> FEATURE:
<223> OTHER INFORMATION: synthetic DNA

<400> SEQUENCE: 17
gtaatcgcac tggagcacac cagcagctgg c                                    31

```
<210> SEQ ID NO 18
<211> LENGTH: 32
<212> TYPE: DNA
<213> ORGANISM: Artificial Sequence
<220> FEATURE:
<223> OTHER INFORMATION: synthetic DNA

<400> SEQUENCE: 18
cgcgccagaa tgtgcggctg cccgaagtaa cc                                    32

<210> SEQ ID NO 19
<211> LENGTH: 30
<212> TYPE: DNA
<213> ORGANISM: Artificial Sequence
<220> FEATURE:
<223> OTHER INFORMATION: synthetic DNA

<400> SEQUENCE: 19
gttgcggact cacgcgacaa tcattcatgg                                       30

<210> SEQ ID NO 20
<211> LENGTH: 31
<212> TYPE: DNA
<213> ORGANISM: Artificial Sequence
<220> FEATURE:
<223> OTHER INFORMATION: synthetic DNA

<400> SEQUENCE: 20
caaggtgaac gactcaaggt tgtgatccca g                                     31

<210> SEQ ID NO 21
<211> LENGTH: 53
<212> TYPE: DNA
<213> ORGANISM: Artificial Sequence
<220> FEATURE:
<223> OTHER INFORMATION: synthetic DNA

<400> SEQUENCE: 21
gaaaatgccg atatgcggcc gcctgcttaa ttaaccagtg tggtgtgcga tcg             53

<210> SEQ ID NO 22
<211> LENGTH: 51
<212> TYPE: DNA
<213> ORGANISM: Artificial Sequence
<220> FEATURE:
<223> OTHER INFORMATION: synthetic DNA

<400> SEQUENCE: 22
cgcctgaata agtgcggccg cccgtggcga aagcaatatc cttctggaac g               51

<210> SEQ ID NO 23
<211> LENGTH: 47
<212> TYPE: DNA
<213> ORGANISM: Artificial Sequence
<220> FEATURE:
<223> OTHER INFORMATION: synthetic DNA

<400> SEQUENCE: 23
ggttaattaa gcaggcgcgc attgtgtgaa gcagttgccg cgcggga                    47

<210> SEQ ID NO 24
<211> LENGTH: 45
<212> TYPE: DNA
<213> ORGANISM: Artificial Sequence
<220> FEATURE:
<223> OTHER INFORMATION: synthetic DNA
```

<400> SEQUENCE: 24
gcttcacaca atgcgcgcct gcttaattaa ccagtgtggt gtgcg      45

<210> SEQ ID NO 25
<211> LENGTH: 30
<212> TYPE: DNA
<213> ORGANISM: Artificial Sequence
<220> FEATURE:
<223> OTHER INFORMATION: synthetic DNA

<400> SEQUENCE: 25
gactggagca caccctgcgt gagtttcacg      30

<210> SEQ ID NO 26
<211> LENGTH: 30
<212> TYPE: DNA
<213> ORGANISM: Artificial Sequence
<220> FEATURE:
<223> OTHER INFORMATION: synthetic DNA

<400> SEQUENCE: 26 cccttttcgat aagacataac ccagcgatgg      30

<210> SEQ ID NO 27
<211> LENGTH: 32
<212> TYPE: DNA
<213> ORGANISM: Artificial Sequence
<220> FEATURE:
<223> OTHER INFORMATION: synthetic DNA

<400> SEQUENCE: 27
cagtaaacgc agggcaatga cgatataccg cc      32

<210> SEQ ID NO 28
<211> LENGTH: 32
<212> TYPE: DNA
<213> ORGANISM: Artificial Sequence
<220> FEATURE:
<223> OTHER INFORMATION: synthetic DNA

<400> SEQUENCE: 28
gcaaccgact gcattatctg gctgaccggg cc      32

<210> SEQ ID NO 29
<211> LENGTH: 52
<212> TYPE: DNA
<213> ORGANISM: Artificial Sequence
<220> FEATURE:
<223> OTHER INFORMATION: synthetic DNA

<400> SEQUENCE: 29
gaaaatgccg atatgcggcc gcatggtcgc tggcagttcc gggtaaccca gg      52

<210> SEQ ID NO 30
<211> LENGTH: 51
<212> TYPE: DNA
<213> ORGANISM: Artificial Sequence
<220> FEATURE:
<223> OTHER INFORMATION: synthetic DNA

<400> SEQUENCE: 30
cgcctgaata agtgcggccg cgcctctacg cgttttaccg acggcggcca g      51

<210> SEQ ID NO 31
<211> LENGTH: 46

<210> SEQ ID NO 31
<211> LENGTH: 46
<212> TYPE: DNA
<213> ORGANISM: Artificial Sequence
<220> FEATURE:
<223> OTHER INFORMATION: synthetic DNA

<400> SEQUENCE: 31
tgctgacccg tgctaacatg aagaccgtg aacgcttcct gaacgc        46

<210> SEQ ID NO 32
<211> LENGTH: 46
<212> TYPE: DNA
<213> ORGANISM: Artificial Sequence
<220> FEATURE:
<223> OTHER INFORMATION: synthetic DNA

<400> SEQUENCE: 32
cacggtcttc catgttagca cgggtcagca gcatttgccc gacgtg        46

<210> SEQ ID NO 33
<211> LENGTH: 28
<212> TYPE: DNA
<213> ORGANISM: Artificial Sequence
<220> FEATURE:
<223> OTHER INFORMATION: synthetic DNA

<400> SEQUENCE: 33
cagcgccttt ttatcatccc cttctcgc        28

<210> SEQ ID NO 34
<211> LENGTH: 30
<212> TYPE: DNA
<213> ORGANISM: Artificial Sequence
<220> FEATURE:
<223> OTHER INFORMATION: synthetic DNA

<400> SEQUENCE: 34
ccatatcgaa catggtgtgg tcgacatagc        30

<210> SEQ ID NO 35
<211> LENGTH: 29
<212> TYPE: DNA
<213> ORGANISM: Artificial Sequence
<220> FEATURE:
<223> OTHER INFORMATION: synthetic DNA

<400> SEQUENCE: 35
ggttgatgaa gctctactgg cgcaaaccc        29

<210> SEQ ID NO 36
<211> LENGTH: 30
<212> TYPE: DNA
<213> ORGANISM: Artificial Sequence
<220> FEATURE:
<223> OTHER INFORMATION: synthetic DNA

<400> SEQUENCE: 36
cggaagatgc cagcactttg caccgattgc        30

<210> SEQ ID NO 37
<211> LENGTH: 50
<212> TYPE: DNA
<213> ORGANISM: Artificial Sequence
<220> FEATURE:
<223> OTHER INFORMATION: synthetic DNA

<400> SEQUENCE: 37
gaaaatgccg atatgcggcc gcgttcctttt accacggcac acctctttgc    50

<210> SEQ ID NO 38
<211> LENGTH: 49
<212> TYPE: DNA
<213> ORGANISM: Artificial Sequence
<220> FEATURE:
<223> OTHER INFORMATION: synthetic DNA

<400> SEQUENCE: 38
cgcctgaata agtgcggccg cagttcatca agggtgaag ttctgctgg    49

<210> SEQ ID NO 39
<211> LENGTH: 46
<212> TYPE: DNA
<213> ORGANISM: Artificial Sequence
<220> FEATURE:
<223> OTHER INFORMATION: synthetic DNA

<400> SEQUENCE: 39
ccattcggtt ccctgcatca atacccaccg gggaaaaacg tttgtc    46

<210> SEQ ID NO 40
<211> LENGTH: 45
<212> TYPE: DNA
<213> ORGANISM: Artificial Sequence
<220> FEATURE:
<223> OTHER INFORMATION: synthetic DNA

<400> SEQUENCE: 40
cggtgggtat tgatgcaggg aaccgaatgg cggaatccct cgacc    45

<210> SEQ ID NO 41
<211> LENGTH: 29
<212> TYPE: DNA
<213> ORGANISM: Artificial Sequence
<220> FEATURE:
<223> OTHER INFORMATION: synthetic DNA

<400> SEQUENCE: 41
gatgcgtgat gataagcagt taacgctgc    29

<210> SEQ ID NO 42
<211> LENGTH: 28
<212> TYPE: DNA
<213> ORGANISM: Artificial Sequence
<220> FEATURE:
<223> OTHER INFORMATION: synthetic DNA

<400> SEQUENCE: 42
cttcaacgta ggcacattcg acaacgcc    28

<210> SEQ ID NO 43
<211> LENGTH: 29
<212> TYPE: DNA
<213> ORGANISM: Artificial Sequence
<220> FEATURE:
<223> OTHER INFORMATION: synthetic DNA

<400> SEQUENCE: 43
gctgtttccg cgatgactac caatgtggc    29

<210> SEQ ID NO 44
<211> LENGTH: 29
<212> TYPE: DNA
<213> ORGANISM: Artificial Sequence

```
<220> FEATURE:
<223> OTHER INFORMATION: synthetic DNA

<400> SEQUENCE: 44
gcgatgataa acgtcgtcgg tactttggc                                              29

<210> SEQ ID NO 45
<211> LENGTH: 50
<212> TYPE: DNA
<213> ORGANISM: Artificial Sequence
<220> FEATURE:
<223> OTHER INFORMATION: synthetic DNA

<400> SEQUENCE: 45
gaaaatgccg atatgcggcc gcgttattga gaaacatgcc tgcgtcacgg                       50

<210> SEQ ID NO 46
<211> LENGTH: 50
<212> TYPE: DNA
<213> ORGANISM: Artificial Sequence
<220> FEATURE:
<223> OTHER INFORMATION: synthetic DNA

<400> SEQUENCE: 46
cgcctgaata agtgcggccg cgacaccatc tttaccaccc ctgctaacgg                       50

<210> SEQ ID NO 47
<211> LENGTH: 42
<212> TYPE: DNA
<213> ORGANISM: Artificial Sequence
<220> FEATURE:
<223> OTHER INFORMATION: synthetic DNA

<400> SEQUENCE: 47
gtttctcaat aacgacacca tctttaccac ccctgctaac gg                              42

<210> SEQ ID NO 48
<211> LENGTH: 43
<212> TYPE: DNA
<213> ORGANISM: Artificial Sequence
<220> FEATURE:
<223> OTHER INFORMATION: synthetic DNA

<400> SEQUENCE: 48
ggtaaagatg gtgtcgttat tgagaaacat gcctgcgtca cgg                             43
```